US009402561B2

(12) United States Patent
Krueger et al.

(10) Patent No.: US 9,402,561 B2
(45) Date of Patent: *Aug. 2, 2016

(54) METHOD AND MAGNETIC RESONANCE APPARATUS FOR DETERMINATION OF PATIENT MOVEMENT DURING DATA ACQUISITION

(75) Inventors: Gunnar Krueger, Schweiz (CH); Arne Littmann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1604 days.

This patent is subject to a terminal disclaimer.

(21) Appl. No.: 11/945,325

(22) Filed: Nov. 27, 2007

(65) Prior Publication Data

US 2008/0214923 A1 Sep. 4, 2008

Related U.S. Application Data

(60) Provisional application No. 60/861,202, filed on Nov. 27, 2006.

(30) Foreign Application Priority Data

Nov. 27, 2006 (DE) .......................... 10 2006 055 933

(51) Int. Cl.
*A61B 5/11* (2006.01)
*A61B 5/055* (2006.01)
(Continued)

(52) U.S. Cl.
CPC .............. *A61B 5/055* (2013.01); *A61B 5/7207* (2013.01); *G01R 33/3415* (2013.01); *G01R 33/5673* (2013.01); *G01R 33/5676* (2013.01); *G01R 33/56509* (2013.01); *A61B 5/11* (2013.01)

(58) Field of Classification Search
CPC .... A61B 5/055; A61B 5/7207; A61B 5/7214; A61B 5/11; G01R 33/3415; G01R 33/56509; G01R 33/5676; G01R 33/5673
USPC .................................................. 600/407, 413
See application file for complete search history.

(56) References Cited

U.S. PATENT DOCUMENTS 4,694,836 A * 9/1987 Buikman et al. .............. 600/410
5,539,312 A * 7/1996 Fu et al. ........................ 324/309
(Continued)

FOREIGN PATENT DOCUMENTS

WO WO 03096050 A1 * 11/2003
WO WO 2006/051911 5/2006

OTHER PUBLICATIONS

"Periodically Rotated Overlapping ParallEL Lines with Enhanced Reconstruction (PROPELLER) MRI; Application to Motion Correction," Pipe, ISMRM 1999, Abstract No. 242 (1999).

*Primary Examiner* — Long V Le
*Assistant Examiner* — Helene Bor
(74) *Attorney, Agent, or Firm* — Schiff Hardin LLP

(57) ABSTRACT

In a method and magnetic resonance (MR) apparatus for determination of movement of an examination subject during the acquisition of (MR) measurement data using at least two antenna elements that exhibit respectively different spatial positions, after each radiated excitation pulse a navigator signal is acquired in the measurement data and movement of the examination subject between two excitation pulses during the acquisition of the measurement data is determined from a change of the signal strength of the navigator signal in the at least two antenna elements and based on the respective spatial positions of the antenna elements.

15 Claims, 3 Drawing Sheets

(56) References Cited

U.S. PATENT DOCUMENTS

| | | |
|---|---|---|
| 5,947,900 A * | 9/1999 | Derbyshire et al. .......... 600/410 |
| 6,292,684 B1 | 9/2001 | Du et al. |
| 6,759,847 B2 | 7/2004 | Brinker et al. |
| 6,771,998 B2 * | 8/2004 | Kirsch .......................... 600/410 |
| 6,842,001 B2 | 1/2005 | Ikezaki |
| 8,624,596 B2 * | 1/2014 | Kannengiesser et al. ..... 324/309 |
| 2005/0036944 A1 | 2/2005 | Van Den Brink et al. |

* cited by examiner

FIG 4 Signal strength
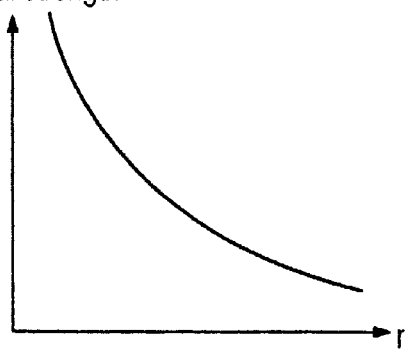
FIG 5 Signal strength
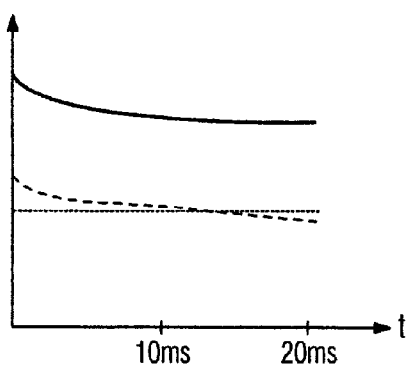
FIG 6
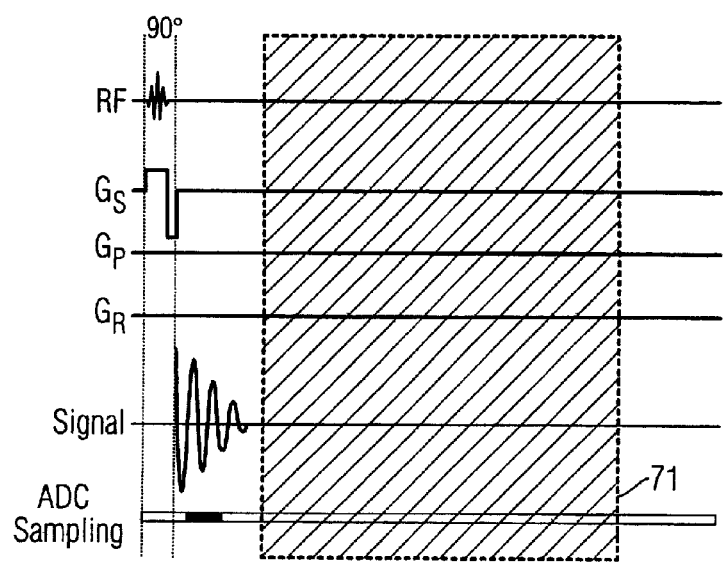

METHOD AND MAGNETIC RESONANCE APPARATUS FOR DETERMINATION OF PATIENT MOVEMENT DURING DATA ACQUISITION

RELATED APPLICATION

The present invention claims the benefit of the filing date of provisional application 60/861,202, filed Nov. 22, 2006.

BACKGROUND OF THE INVENTION

1. Field of the Invention

The present invention concerns a method for determination of movement by an examination subject during the acquisition of magnetic resonance measurement data. Furthermore, the invention concerns a magnetic resonance apparatus that implements such a method.

2. Description of the Prior Art

Magnetic resonance (MR) technology is a known modality with which images of the inside of an examination subject can be generated. For this purpose, the examination subject is positioned in a strong, static, homogeneous basic magnetic field (field strengths of 0.2 Tesla to 7 Tesla and more) in an MR apparatus such that nuclear spins in the subject orient along the basic magnetic field. Radio-frequency excitation pulses are radiated into the examination subject to trigger nuclear magnetic resonances, the triggered nuclear magnetic resonances being measured and MR images being reconstructed therefrom. Rapidly-switched magnetic gradient fields are superimposed on the basic magnetic field for spatial coding of the measurement data. The acquired measurement data are digitized and stored as complex number values in a k-space matrix. An MR image can be reconstructed from the k-space matrix populated with these values by means of a multi-dimensional Fourier transformation.

Due to its relatively long measurement time, the MR imaging is movement-sensitive, meaning that movement of the examination subject during the acquisition of the measurement data can contribute to significant limitations in the image quality.

Various methods therefore exist that seek to detect movement of the examination subject and to use the acquired information either for improved reconstruction of the image, or for a prospective adaptation of the measurement system for the subsequent acquisition of measurement data.

Somewhat elaborate methods of this type utilize external markers and structural systems with which movement can be detected with optical means three-dimensionally in space and taken into account. Such methods require additional hardware and thus incur a high cost expenditure, so that such methods are not typically used.

Moreover, methods are known in which a special design of the measurement sequence enables the movement detection. Given the acquisition of the measurement data in the PROPELLER technique (as it described, for example, in the document by J. G. Pipe, "Periodically Rotated Overlapping Parallel Lines with Enhanced Reconstruction (PROPELLER) MRI; Application to Motion Correction", ISMRM 1999, Abstract Nr. 242), a k-space matrix is scanned in segments, with the individual k-space segments being rotated relative to one another so that a central k-space region is scanned with each k-space segment. The sub-sampling of the central k-space region enables a movement that occurs between the scanning of the individual k-space segments to be detected and to be taken into account in the image reconstruction.

Another method is used in functional MR imaging (fMRI") and is known under the name PACE (for "prospective acquisition correction"). Sequential, complete multi-slice single-shot EPI (for "echo planar imaging") data sets of the brain are acquired while various stimuli are presented to a subject. In order to be able to compare the repeatedly acquired data sets with one another, it is necessary that the three-dimensional data sets be positioned and aligned identically relative to one another. In the PACE method a data set is evaluated in the acquisition of the measurement data to allow the acquisition of the following data set to ensue dependent on any change in the position of the examination subject that may have occurred.

The above-described methods are tailored to the special design of the employed measurement sequence, and typically cannot be transferred to other measurement sequences.

A different method used in many cases for detection and/or for correction of movements occurring during the acquisition of the measurement data is the use of what are known as navigator signals (also called navigator echoes).

In this type of acquisition, additional data (known as navigator signals) are acquired in addition to the actual measurement data with which the k-space matrix corresponding to the image to be produced is populated. These navigator signals allow a movement of the examination subject that occurs during the acquisition of the measurement data to be detected and allow this to be taken into account if applicable in the reconstruction of the MR image or images, such that movement artifacts occur to a lesser extent.

A small region of the k-space matrix (for example one k-space line or a small central section of the k-space matrix) is typically scanned by the navigator signal. Movement that may possibly have occurred between the scanning of the two navigator signals can be detected and/or taken into account in the image reconstruction by a comparison of the k-space values scanned by the navigator signal with regard to their amplitude and phase position.

Depending on the complexity of the navigator signal, the measurement duration of a measurement sequence sometimes increases significantly due to the acquisition of such navigator signals.

A need therefore exists to improve methods of the type wherein a possible movement of an examination subject is detected with the aid of navigator signals.

SUMMARY OF THE INVENTION

An object of the present invention is to provide a method for determination of a movement of a subject to be examined during the acquisition of measurement data of a magnetic resonance data set that requires less measurement and calculation time and that can be used in many measurement sequences. Furthermore, it is the object of an invention to provide an MR apparatus with which a movement of a subject to be examined during the acquisition of measurement data of a magnetic resonance data set can be detected with simultaneously a smaller measurement and calculation time increase and with more versatile usability.

The above objects are achieved in accordance with the invention by a method for determination of movement of an examination subject during the acquisition of measurement data of a magnetic resonance data set using at least two antenna elements that at different spatial positions with the acquisition of the measurement data after each radiated excitation pulse including a navigator signal, and wherein movement of the examination subject between two excitation pulses during the acquisition of the measurement data is determined from a change of the signal strength of the navigator signal in the at least two antenna elements, taking into consideration the spatial position of the antenna elements.

In the inventive method, the strength of the navigator signal is measured in relation to the spatial position of the various antenna elements. In contrast to conventional methods in which a section of a k-space matrix is scanned with a navigator signal and the amplitude and phase values resulting from this are evaluated, according to the invention the navigator signal can merely be evaluated with regard to its signal strength, such that the acquisition of the navigator signal can ensue in a relatively fast and simple manner. The relatively small data set (data quantity) of the navigator signal that is necessary for the determination of the movement of an examination subject according to the inventive method allows an efficient and fast calculation of the movement parameters so that the measurement sequence is only insignificantly limited in terms of its performance. The acquisition of the navigator signal can be implemented within 10 ms or less (such as, for example, within 5 ms or less), in any case within less than 100 ms, such that the measurement time of the sequence is only insignificantly influenced.

The respective spatial sensitivity profiles of the at least two antenna elements are advantageously taken into account in the determination of the movement of the examination subject. The determination of the movement of the examination subject can thereby ensue more precisely.

The navigator signals preferably are acquired immediately after a refocusing pulse that is emitted for one of the excitation pulses. At this point in time a relatively strong nuclear magnetic resonance signal can be measured, such that here the acquisition of the navigator signal can ensue with a good signal-to-noise ratio. Furthermore, no acquisition of data that code the actual image information occurs at this point in time in most typically employed measurement sequences, so that already-existing measurement sequences can be expanded by the acquisition of a navigator signal so that the inventive method can be implemented in the expanded measurement sequences.

The navigator signals are preferably acquired without radiation of gradient fields. Such an implemented acquisition can be integrated without problems into known measurement sequences, since no gradient fields need to be switched for acquisition of the navigator signals, that would otherwise have to be matched with other gradient fields that are switched during the measurement sequence. The navigator signal acquisition thus can ensue with a very good signal-to-noise ratio.

In an advantageous embodiment, the position of the nuclear spins excited to resonance in the examination subject by the excitation pulse relative to the spatial position of the antenna elements is additionally taken into account in the determination of movement of the examination subject. It is also then possible to detect movement in a correct manner when the MR examination follows no standard protocol in which, for example, the position of an excited volume (for example a slice) is known in advance in comparison to the spatial position of the at least two antenna elements, and the determination of the movement of the examination subject has been matched with (referenced to) this. In this embodiment the orientation of a slice can now also be arbitrarily selected, for example, and the determination of the movement of the examination subject can be flexibly matched therewith.

The inventive magnetic resonance apparatus has a control unit that is fashioned for implementation of the method described above.

BRIEF DESCRIPTION OF THE DRAWINGS

FIG. 4 illustrates the spatial sensitivity profile of an antenna element.

FIG. 5 illustrates the measured signal strength in one of the antenna elements before and after a movement of the head to be examined.

FIG. 6 is a diagram of a schematically indicated pulse sequence in which the acquisition of the navigator signals ensues after a refocusing pulse.

DESCRIPTION OF THE PREFERRED EMBODIMENTS

Figure 1:
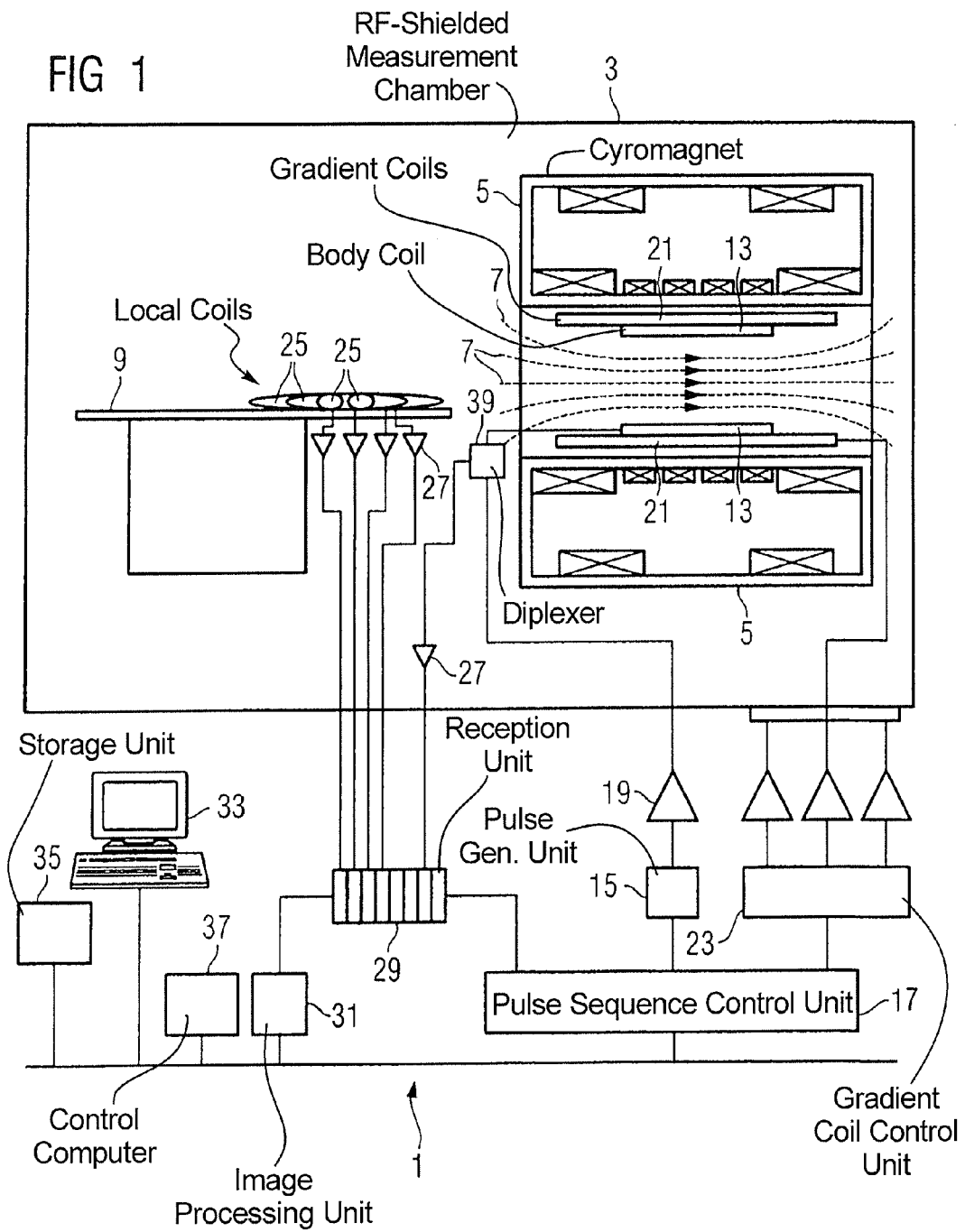
FIG. 1 schematically illustrates the basic design of an MR apparatus.

FIG. 1 schematically shows the basic components of a magnetic resonance apparatus 1. In order to examine a body by means of magnetic resonance imaging, various magnetic fields matched as precisely as possible with one another in terms of their temporal and spatial characteristics are applied.

A strong magnet (typically a cryomagnet 5 with a tunnel-shaped opening) arranged in a radio-frequency-shielded measurement chamber 3 generates a static, strong basic magnetic field 7 that is typically 0.2 Tesla to 3 Tesla and more. A body or a body pat to be examined (not shown here) is supported on a patient bed 9 and positioned in a homogeneous region of the basic magnetic field 7.

The excitation of the nuclear spins of the body ensues by radio-frequency excitation pulses that are radiated from a radio-frequency antenna (shown here as a body coil 13). The electrical signals representing radio-frequency excitation pulses are generated by a pulse generation unit 15 that is controlled by a pulse sequence control unit 17. After an amplification by a radio-frequency amplifier 19, they are conducted to the radio-frequency antenna. The radio-frequency system shown here is only schematically indicated. More than one pulse generation unit 15, more than one radio-frequency amplifier 19 and multiple radio-frequency antennas are typically used in the magnetic resonance apparatus 1.

Furthermore, the magnetic resonance apparatus 1 has gradient coils 21 with which magnetic gradient fields for selective slice excitation and for spatial coding of the measurement signal are radiated in a measurement (data acquisition). The gradient coils 21 are controlled by a gradient coil control unit 23 that, like the pulse generation unit 15, is connected with the pulse sequence control unit 17.

The signals emitted by the excited nuclear spins are received by the body coil 13 and/or by local coils 25, amplified by associated radio-frequency preamplifiers 27 and further processed and digitized by a reception unit 29.

From RF coil that can be operated both in transmission mode and in reception mode, such as (for example) the body coil 13, the correct signal relaying is regulated by an upstream transmission-reception diplexer 39.

An image processing unit 31 generates from the measurement data an image that is presented to a user at a control console 31, or is stored in a storage unit 35. A central computer 37 controls the individual system components. The computer 37 is fashioned (programmed) to implement the inventive method.

Figure 2:
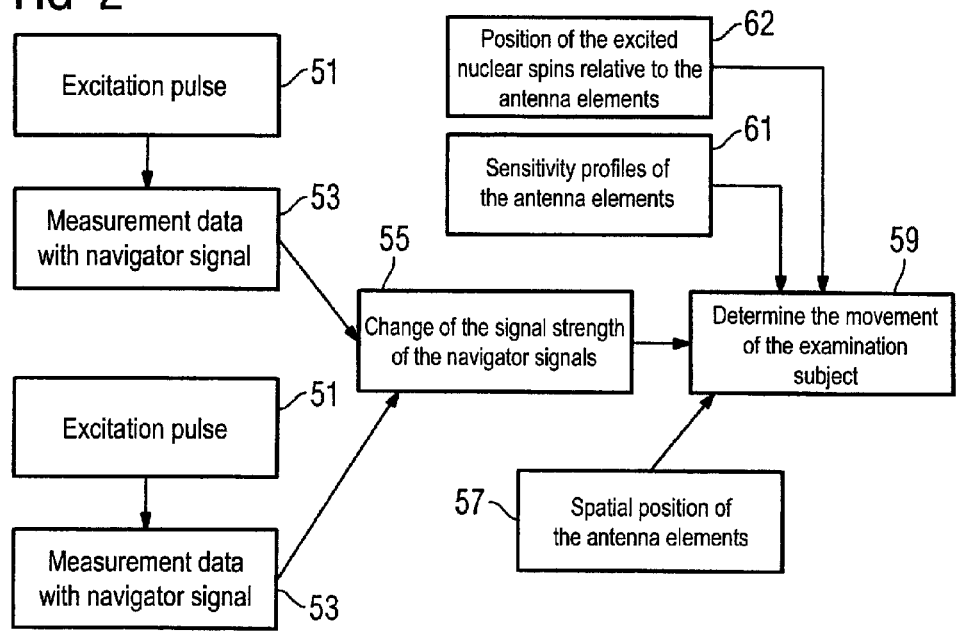
FIG. 2 is a schematic overview of an embodiment of the inventive method.

FIG. 2 shows a schematic overview of an embodiment of the inventive method. As is typical in MR technology, the acquisition of the measurement data 53 ensues after radiation of an excitation pulse 51 that triggers nuclear magnetic resonance signals in the examination subject. In order to be able to determine a change of the position of the examination subject that may have occurred between two excitation pulses 51 radiated at different points in time, the acquisition of the subsequent measurement data 53 includes a navigator signal.

The acquisition of the measurement data 53 ensues with at least two antenna elements that exhibit respectively different spatial positions. A position change of the examination subject between the two excitation pulses 51 necessarily involves a change of the spatial position of the examination subject relative to the at least two antenna elements. This causes a change 55 of the signal strength of the respective navigator signals acquired after the excitation pulses 51. A determination 59 of any movement of the examination subject that has occurred ensues from this change 55, together with the (known) spatial position 57 of the antenna elements.

The sensitivity profiles 61 of the antenna elements can likewise be taken into account in the determination 59 of the movement of the examination subject, so the determination 59 of the movement of the examination subject can ensue more precisely. A position 62 of the nuclear spins excited to resonance in the examination subject by the excitation pulse relative to the spatial position 57 of the antenna elements can likewise be taken into account in the determination 59 of the movement of the examination subject, which is particularly advantageous given the use of non-standardized examination protocols wherein the position of the volume of the excited nuclear spins (for example their slice position/orientation is freely selectable).

The inventive method can be used in the most varied types of sequences. The method can be used when a k-space matrix associated with an MR image is scanned in segments, by virtue of the measurement data 53 of a k-space segment being respectively scanned after each excitation pulse 51. The method can also be used when a number of MR images are produced immediately sequentially, so movement that may have occurred between two successive MR images can be detected by the inventive method.

The information acquired through the determination 59 of movement of the examination subject can be used in various ways. For example, this information can be used to reduce movement artifacts in the reconstruction of MR images from the acquired measurement data 53. The information also can be used in a prospective manner by adapting (modifying) the measurement sequence to the changed position of the examination subject after the detection of movement. Measurement data 53 then are generated in the acquisition that already allow MR images to be reconstructed that exhibit fewer movement artifacts, or that are already aligned substantially with one another for further processing.

Figure 3:
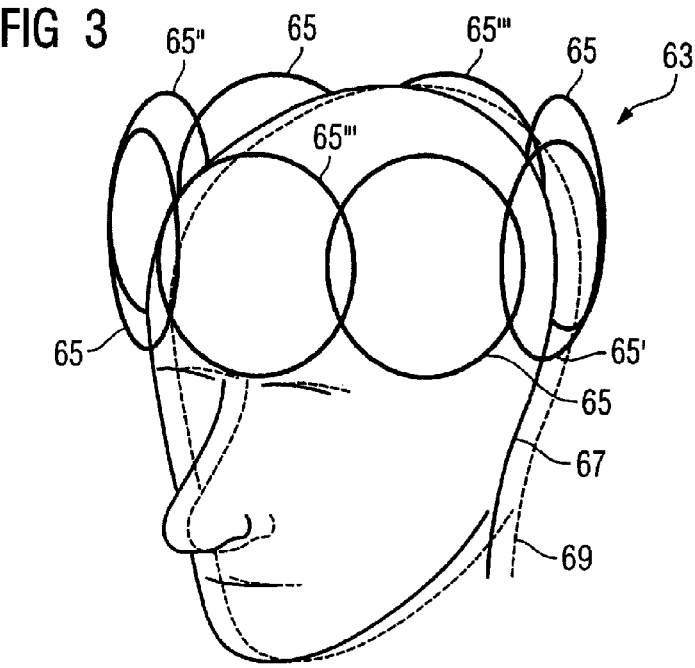
FIG. 3 shows the head of a patient to be examined who is positioned in an antenna array having multiple antenna elements.

FIG. 3 shows an exemplary application of the inventive method for the imaging of a brain. The acquisition of the measurement data 53 ensues with an antenna array 63 that has eight individual antenna elements 65 that respectively exhibit a different spatial positions. The head 67 of a patient to be examined is positioned in the antenna array 63. A possible position change 69 of the head 67 during the acquisition of the measurement data is indicated by the dashed representation.

FIG. 4 schematically shows the sensitivity profile of an antenna element 65. The signal strength that is provoked in the antenna elements 65 by a subject is plotted with respect to the distance r of the subject relative to the antenna element 65. The further removed that the subject is from the antenna element 65, the lower the strength of the signal induced in the antenna element 65. This means that the signal strength of the navigation signal that is measured by an antenna element 65 changes when an examination subject moves relative to the antenna element 65, as is shown in FIG. 5. The solid line corresponds to the signal strength of a navigator signal for a specific position of the head 67 of the patient; the dashed line corresponds to the signal strength of an equivalent navigator signal after a position change 69 of the head 67.

When a movement of the head 67 toward its left side ensues as shown in FIG. 3, according to the embodiments in FIG. 4 and FIG. 5 the strength of the navigator signal will increase to its strongest in the antenna element 65' arranged at the left ear, while the strength of the navigator signal will distinctly fall in the antenna element 65" arranged at the right ear. The strength of the navigator signal will remain essentially unchanged in the front and rear antenna elements 65'''; the increase or decrease of the strength of the navigator signal will be less strongly pronounced in the remaining antenna elements arranged at angles than in these lateral antenna elements.

This change of the signal strength can now be quantitatively evaluated to determine in real time the movement that has occurred, from the change of the signal strength of the navigator signal, by means of mathematical calculations. Alternatively it is possible to compare the change of the signal strength with previously measured and stored alteration patterns that have been caused by different movement patterns, and thus to determine the movement.

FIG. 6 shows the schematic design of a preferred measurement sequence in which the acquisition of the measurement data after an excitation pulse includes the acquisition of a navigator signal that, in the inventive method, is used for determination of a movement of an examination subject.

Radiated radio-frequency excitation pulses RF (here, for example, a 90° excitation pulse) are shown in the first line. The following three lines characterize the applied gradient fields $G_S$, $G_P$ and $G_R$ in the slice direction S, phase coding direction P and readout direction R, respectively. A slice-selection gradient is shown that is applied in the slice direction S during the 90° excitation pulse, with a subsequent refocusing pulse. It is thereby achieved that only nuclear spins that are located in a specific slice of the examination subject are excited to resonances. The following line shows the magnetic resonance signals (SIGNAL) induced in an examination subject. The points in time at which an acquisition of the measurement signal ensues by scanning of the magnetic resonance signals are shown as black bars in a last line (ADC Sampling). The shown black bars 73 characterize the acquisition of the navigator signal, which ensues a few milliseconds after the end of the slice refocusing.

The shown measurement sequence is only the beginning thereof, in which the acquisition of the navigator signal is shown with which the induced nuclear magnetic resonances that are measured after a gradient field with a refocusing pulse has been switched (activated) during an excitation pulse. The further course of the measurement sequence (indicated by a grey rectangle 71) is not significant for the inventive method and can be fashioned in the most varied ways.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining movement of an examination subject during acquisition of magnetic resonance (MR) measurement data comprising:

radiating an examination subject with at least two excitation pulses that each excite nuclear spins in the subject causing emission of magnetic resonance signals from the subject;

with at least two antenna elements respectively located at different spatial positions, acquiring after each excitation pulse, measurement data comprising said magnetic resonance signals and a navigator signal exhibiting a navigator signal strength that, when said navigator signal is detected by said at least two antenna elements, is dependent on respective distances between a region of the examination subject from which the navigator signal originates and the respective different spatial positions of said at least two antenna elements; and providing said navigator signals to a computerized processor without conversion of the respective navigator signals detected at said at least two antenna elements into k-space values and, in said processor automatically electronically determining whether movement of the examination subject has occurred between said two excitation pulses solely by detecting a change of said navigator signal strength of the respective navigator signals respectively as acquired at said at least two antenna elements, and analyzing the detected change dependent on the respective spatial positions of the at least two antenna elements.

2. A method as claimed in claim 1 wherein each of said at least two antenna elements has a spatial sensitivity profile associated therewith, and comprising automatically electronically determining said movement of the examination subject additionally dependent on the respective spatial sensitivity profiles.

3. A method as claimed in claim 1 comprising acquiring said navigator signals directly after a refocusing for one of said excitation pulses.

4. A method as claimed in claim 1 comprising acquiring said magnetic resonance signals without radiation of gradient fields into the examination subject.

5. A method as claimed in claim 1 comprising determining said movement additionally dependent on a position of nuclear spins excited to resonance in the examination subject by each excitation pulse, relative to the respective spatial positions of the antenna elements.

6. A method as claimed in claim 1 wherein said examination subject, during acquisition of said measurement data, is moving away from one of said antenna elements, and comprising analyzing said change of said navigator signal strength of the respective navigator signals by analyzing a decay of said signal strength of the navigator signal acquired by said one of said antenna elements.

7. A method as claimed in claim 1 comprising acquiring the respective navigator signals with a time interval of 100 ms or less therebetween.

8. A method as claimed in claim 1 comprising acquiring the respective navigator signals with a time interval of 10 ms or less therebetween.

9. A method as claimed in claim 1 comprising acquiring the respective navigator signals with a time interval of 5 ms or less therebetween.

10. A magnetic resonance apparatus comprising:

a data acquisition unit configured to receive an examination subject therein to acquire magnetic resonance measurement data from the examination subject;

a radio-frequency antenna in said data acquisition unit that emits at least two excitation pulses into the examination subject that each excite nuclear spins in the examination subject that cause magnetic resonance signals to be emitted from the examination subject;

at least two reception coil elements located at respectively different spatial positions in the data acquisition unit that acquire measurement data after each excitation pulse comprising said magnetic resonance signals and a navigator signal exhibiting navigator signal strength that, when said navigator signal is detected by said at least two antenna elements, is dependent on respective distances between a region of the examination subject from which the navigator signal originates and the respective different spatial positions of said at least two antenna elements; and a computerized control computer supplied with said measurement data without conversion of the respective navigator signals detected at said at least two antenna elements into k-space values, said control computer being configured to determine whether movement of the examination subject has occurred between said two excitation pulses solely by detecting a change in said navigator signal strength of the respective navigator signals acquired at said at least two reception antenna elements, and analyzing the detected change dependent on the respective spatial positions of said at least two reception antenna elements.

11. A magnetic resonance apparatus as claimed in claim 10 wherein one of said at least two reception antenna elements is operated as said transmission antenna.

12. An apparatus as claimed in claim 10 wherein said examination subject, during acquisition of said measurement data, is moving away from one of said antenna elements, and wherein said computerized control computer is configured to determine said change of said navigator signal strength of the respective navigator signals by analyzing a decay of said signal strength of the navigator signal acquired by said one of said antenna elements.

13. An apparatus as claimed in claim 10 wherein said data acquisition unit is configured to acquire the respective navigator signals with a time interval of 100 ms or less therebetween.

14. An apparatus as claimed in claim 10 wherein said data acquisition unit is configured to acquire the respective navigator signals with a time interval of 10 ms or less therebetween.

15. An apparatus as claimed in claim 10 wherein said data acquisition unit is configured to acquire the respective navigator signals with a time interval of 5 ms or less therebetween.

* * * * *